US005474193A

United States Patent [19]

Larsson et al.

[11] Patent Number: 5,474,193

[45] Date of Patent: Dec. 12, 1995

[54] BREASTFEEDING ASSISTANCE DEVICE

[75] Inventors: Karl O. A. H. Larsson, Zug, Switzerland; Gotthilf Weniger; Brian Silver, both of Cary, Ill.

[73] Assignee: Medela, Inc., McHenry, Ill.

[21] Appl. No.: 396,251

[22] Filed: Feb. 28, 1995

Related U.S. Application Data

[63] Continuation of Ser. No. 272,269, Jul. 8, 1994, abandoned, which is a continuation of Ser. No. 866,896, Mar. 26, 1992, abandoned, which is a continuation-in-part of Ser. No. 815,375, Dec. 31, 1991, abandoned.

[51] Int. Cl.$^{6}$ .................................................. A61M 37/00

[52] U.S. Cl. ......................... 215/11.4; 215/11.5; 224/148

[58] Field of Search .................................. 215/11.4, 11.5, 215/11.1; 606/234, 235, 236, 158, 157; 604/407; 128/DIG. 6, DIG. 24; 224/148, 194, 202, 250, 257, 258

[56] References Cited

U.S. PATENT DOCUMENTS

| | | | |
|---|---|---|---|
| 147,909 | 2/1874 | Curtiss . | |
| D. 276,939 | 12/1984 | Pascoe | 606/234 X |
| 279,935 | 6/1883 | Glattsteine . | |
| 682,464 | 9/1901 | Graham-Yooll . | |
| 696,328 | 3/1902 | Graham-Yooll . | |
| 2,313,219 | 3/1943 | Bulling . | |
| 2,328,569 | 9/1943 | McGraw . | |
| 2,372,281 | 3/1945 | Jordan . | |
| 2,597,483 | 5/1952 | Head, Sr. | 215/11.4 X |
| 2,697,531 | 12/1954 | Hood . | |
| 2,708,421 | 5/1955 | Jauch . | |
| 2,756,740 | 7/1956 | Deane . | |
| 2,760,664 | 8/1956 | D'Amico et al. . | |
| 2,775,240 | 12/1956 | Morrisey et al. . | |
| 2,853,069 | 9/1958 | Beacham et al. . | |
| 2,883,985 | 4/1959 | Evans . | |
| 2,907,539 | 10/1959 | Vandan | 224/148 |
| 2,923,296 | 2/1960 | Adams et al. . | |
| 2,969,064 | 1/1961 | Metz . | |
| 3,086,525 | 4/1963 | Whitcomb . | |
| 3,144,230 | 8/1964 | Brooks | 224/148 |
| 3,263,848 | 8/1966 | Zackheim | 215/11.1 |
| 3,426,755 | 2/1969 | Clegg . | |
| 3,641,999 | 2/1972 | Greene | 128/DIG. 24 X |
| 3,645,262 | 2/1972 | Harrigan | 215/11.1 X |
| 3,757,784 | 9/1973 | Avery | 215/11.1 X |
| 3,945,524 | 3/1976 | Tkacivkas | 215/11.1 |
| 3,977,638 | 8/1976 | Woodard . | |
| 3,990,597 | 11/1976 | Barton . | |
| 4,153,170 | 5/1979 | Aquarian | 215/11.1 |
| 4,687,466 | 8/1987 | Larsson | 215/11.4 X |
| 4,765,037 | 8/1988 | Perry | 24/301 |
| 4,776,546 | 10/1988 | Goldson et al. | 224/148 |
| 4,929,229 | 5/1990 | Larsson | 604/74 |
| 4,990,157 | 2/1991 | Roberts et al. | 606/236 X |

FOREIGN PATENT DOCUMENTS

| | | | |
|---|---|---|---|
| 7673 | of 1886 | United Kingdom . | |
| 2169210 | 7/1986 | United Kingdom | 215/11.4 |

*Primary Examiner*—Stephen J. Castellano
*Attorney, Agent, or Firm*—Willian Brinks Hofer Gilson & Lione

[57] ABSTRACT

A compact preferably disposable device is disclosed for providing a suckling infant with a liquid diet supplement simultaneously with normal breastfeeding. The device includes a container for holding the supplement and a fluid delivery mechanism adapted to fit onto the container. The fluid delivery mechanism comprises a flexible teat, an elongated flexible tube and a valve mechanism. The flexible tube extends into the teat and is in fluid communication with the interior of the teat, with the other end of the tube sized to fit into the infant's mouth simultaneously while breastfeeding. A tubing clamp carried by the tubing having a notch into which the tubing can be wedged to pinch it closed is also advantageously provided.

10 Claims, 1 Drawing Sheet

BREASTFEEDING ASSISTANCE DEVICE

This application is a continuation of application Ser. No. 08/272,269, filed Jul. 8, 1994, abandoned, which is a continuation of application Ser. No. 07/866,896, filed Mar. 26, 1992, abandoned, which is a continuation-in-part of U.S. Ser. No. 07/815,375 filed Dec. 31, 1991, abandoned.

FIELD OF THE INVENTION

This invention relates to improvements to devices used to provide a diet supplement to a suckling child simultaneously with normal breastfeeding, that is feeding at the breast.

BACKGROUND OF THE INVENTION

There are many instances when the amount of milk which a suckling infant is receiving from the breast needs to be augmented. For instance, some babies have difficulty in learning to suckle the breast. This can lead to a reluctance to breastfeed, since the infant does not receive immediate gratification upon suckling. The mother's milk supply may also be inadequate, such as from temporary reduction in milk supply from mother-baby separation, illness or the like.

It is also possible for an adoptive mother to induce lactation. The mammary glands can be stimulated to begin to produce milk. The induction of lactation can take some time, however. Moreover, most women will not be able to exclusively breastfeed the adopted child.

While the milk supply can be supplemented in these instances by bottle feeding, it is most desirable to be able to provide the diet supplementation simultaneously with normal breastfeeding. This serves to stimulate the production of more milk, improves suckling when necessary, and further perpetuates the mother-child bonding incident to breastfeeding.

There are a number of considerations in designing a device to so supplement the milk supply during breastfeeding. First, it should deliver the supplement to the infant in an unobtrusive manner. The user should also be comfortable with the device, and be able to use it with relative ease.

The child must also be able to get the breast nipple and the supplement delivery means into its mouth simultaneously. A small diameter delivery tube can be used to this end.

One supplement delivery device which meets the foregoing objectives is disclosed in U.S. Pat. No. 4,687,466. That device has proven quite satisfactory, but in its commercial form is larger in size than is most desirable for the greatest ease in portability, where portability may be another consideration. The '466 device is also not specifically designed to be disposable after use, being made in its commercial form very durable for cleaning and reuse. The fluid delivery mechanism of the '466 device as commercialized is furthermore not particularly adapted for use with other supplement containers such as standard milk bottles.

SUMMARY OF THE INVENTION

It is a principal objective of the present invention to provide an improved breastfeeding assistance device which is easily used to supplement the user's milk supply simultaneously with normal nursing, which is comfortable for the user, and which is very compact for ease in carrying. Another objective of the invention is to provide an improved breastfeeding assistance device which is inexpensive enough to be rendered disposable in the mind of the user. Yet a further objective of the invention is to provide an improved valving and fluid delivery mechanism for a breastfeeding assistance device, and which fluid delivery mechanism may furthermore be used with a standard milk bottle, volumetric feeder or the like.

These and other objectives have been realized in the present invention which comprises a preferably compact container for holding the liquid breastfeeding supplement, and a fluid delivery mechanism adapted to fit on the container. The fluid delivery mechanism comprises a flexible teat and a one-way valve which allows for liquid supplement outflow from the container, but closes the container against backflow.

The container can take the form of a small cylindrical bottle with an open top or mouth at one end. In its preferred form disclosed herein, the container is a small (e.g., about 80 ml volume) rigid plastic bottle. The fluid delivery mechanism is attached to the bottle mouth to close the bottle opening. In this preferred form, the flexible teat is formed integral with a collar, the latter being match-threaded with the end of the bottle adjacent the bottle mouth.

A small diameter elongated flexible tube extends into the flexible teat. The tube is designed so that its other end can be located adjacent a breast nipple, so that it easily fits into the infant's mouth along with the breast nipple.

The valve device between the bottle opening and the flexible teat comprises a rigid disk-shaped base having one or more apertures, with the base being sized to be received on the lip of the bottle mouth to thereby close the bottle opening. A flexible member covers the aperture(s) in the manner of a flap valve, and is advantageously attached to the base by means of a portion (knob) extending from the member which is received in an aperture of the base.

The flexible teat has the advantage that the device can be "primed" by squeezing the teat to fill it with supplement. The flexible teat furthermore allows for the mother to force supplement into the infant's mouth by squeezing the teat.

The fluid delivery mechanism, particularly when teat and collar are integrally molded, can be made inexpensively enough to be sold as disposable. It can further be adapted for use with standard milk bottles, including collapsible bag-type milk bottles.

In keeping with the very compact nature of the present device, the disclosed embodiment also provides a clip attached to the container, as by a rubber band, for use in suspending the breastfeeding supplement device from an article of clothing, for example. A tubing clamp is also advantageously provided for use in cutting off supplement flow.

The tubing clamp is carried on the tubing itself, and is preferably formed of a substantially flat member having two apertures through which the elongated tubing is threaded. The member can be slid along the tubing via the threaded engagement provided through the apertures. A v-shaped notch is provided on a portion of the clamp which is sized so that the tubing can be pinched closed.

The foregoing features and advantages of the present invention will be further understood upon consideration of the following detailed description of an embodiment of the invention taken in conjunction with the accompanying drawings, in which:

DETAILED DESCRIPTION OF AN EMBODIMENT THE INVENTION

Figure 1:
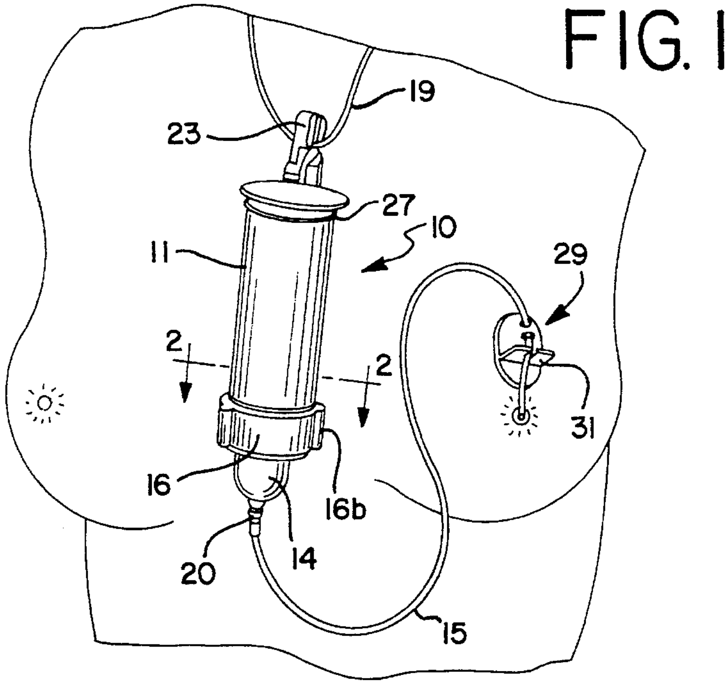
FIG. 1 is an elevational view of a breastfeeding supplement device made in accordance with the teachings of the present invention positioned on a user's chest.
Figure 3:
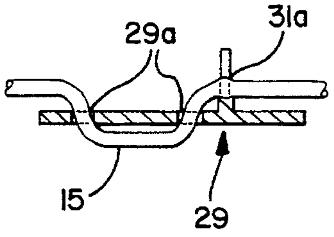
FIG. 3 is an enlarged cross-sectional view of the tubing clamp shown in FIG. 1
Figure 2:
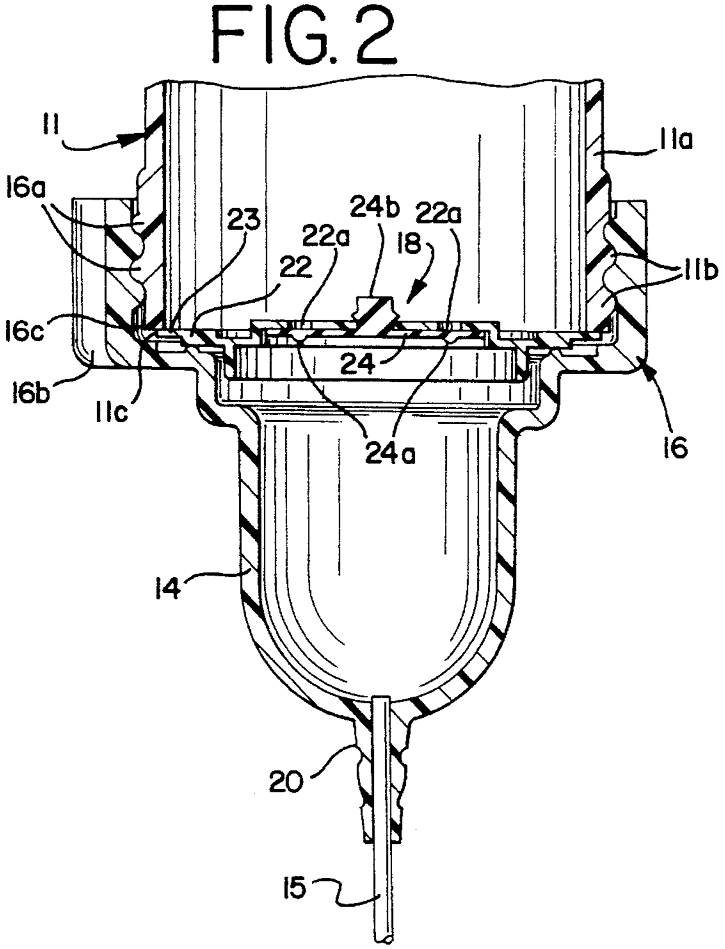
FIG. 2 is an enlarged sectional view taken along line 2—2 of FIG. 1.
Figure 4:
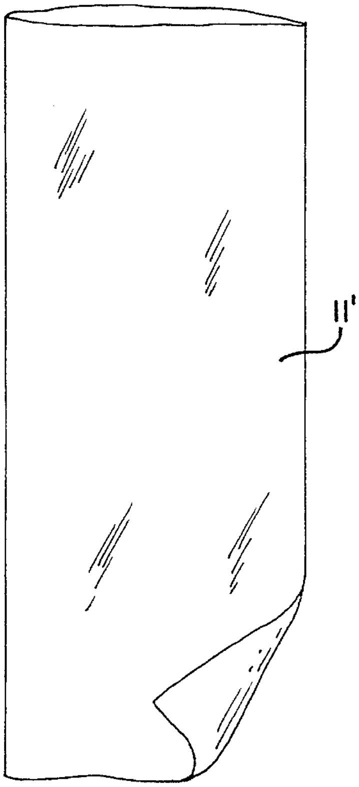
FIG. 4 is a ubiquitous collapsible milk bag.

Referring to FIG. 1, the supplemental nursing device 10 has a container 11 in the form of a rigid semi-transparent plastic bottle having a neck or top portion 11*a*. The container 11 may also be a collapsible bag-type milk bottle 11' of any type well known in the art and available commercially, as shown in FIG. 4. The container 11 is otherwise closed except for a bottle opening, or mouth, defined by the neck 11*a*. Exterior threads 11*b* are formed around the bottle neck adjacent the mouth. Gradations can be provided on the container exterior to assist in measuring liquid supplement. An 80 ml bottle is disclosed.

A fluid delivery mechanism is attached to the neck 11*a* by an attachment ring or collar 16 having interior threads 16*a* which are match-threaded with the threads 11*b*. Gripping protrusions 16*b* are provided for ease in turning. The fluid delivery mechanism includes a flexible teat 14 and a valve device 18. The valve device is seated on the rim 11*c* of the neck defining the bottle mouth, as will be described in more detail hereafter.

The flexible teat 14 has an elongated tubular segment 20 which extends from the end of the flexible teat 14. One end of an elongated flexible tube 15 is received within the tubular segment 20, and fixed therein. Alternatively, the tubing could extend directly through an opening in the teat, with some other form of strain relief for the tubing/teat interconnection. The tubing is of sufficient length to enable the user to position the other end of the tubing 15 adjacent a breast nipple (FIG. 1). A piece of medical adhesive tape (not shown) may be advantageously used to position this free end of the tubing. It will be noted that a sufficient length of tubing 15 can also be provided to allow the tubing to be looped and placed directly on the breast. Supplement is thereby warmed by body-heat as it passes through the tubing 15.

The tubing 15 is of a small size and its free end readily fits unobtrusively within the infant's mouth along with the breast nipple. The tubing 15 may also be provided in different internal diameters for various fluid delivery mechanisms. The internal diameter of the tubing in the disclosed embodiment is 0.75 mm and about 45 Shore A hardness.

The flexibility of the teat 14 allows for the tubing 15 to be easily primed for the suckling infant by squeezing the teat 14. Moreover, the amount of liquid supplement delivered through the tubing 15 to an infant may easily be increased if the infant's suckling is insufficient to create a satisfactory flow by squeezing the flexible teat 14. The teat of the disclosed embodiment is formed with about 85 Shore A hardness.

The valve device 18 includes a disk-shaped base 22 which has a plurality of apertures 22*a*. The base 22 is sized to sit on the rim 11*c* of the bottle mouth.

The base 22 fits within a shoulder 16*c* formed by the attachment ring 16. It will be noted that the attachment ring 16 and the flexible teat 14 are formed integral, as by molding. When the attachment ring 16 is screwed onto the container, the shoulder forces the base 22 against the rim 11*c* of the mouth, substantially closing the bottle opening. A small channel (23) is formed in the base 22 in the area which overlies the rim 11*c* to permit air to enter the bottle in response to the withdrawal of supplement. The threaded engagement between the attachment ring and bottle is loose enough to permit air to reach this channel. Alternatively, the threads can be broken to assure an air path.

A flexible disk-shaped member 24 in the form of a thin flexible membrane with reinforcing bosses 24*a* is in facial engagement with the base 22 and covers the apertures 22*a*, to control the flow of liquid supplement from the container 11 into the teat 14. The flexible disk member 24 is substantially identical to that disclosed in U.S. Pat. No. 4,929,229, the disclosure of which is herein incorporated by reference, and functions in the same manner as in that patent to control liquid flow. The flexible disk member 24 is attached to the base 22 by a knob 24*b* which extends outwardly from the flexible disk member and is fit through an aperture in the base 22.

In use, the valve device 18 operates as a flap valve, allowing air to enter the container 11 in response to the removal of liquid supplement caused by suckling (via the airflow path through the threads and base, discussed above), but not allowing for liquid supplement to flow back into the container 11 from the teat.

The fluid delivery mechanism can be cleaned by putting a cleaning solution in the container 11 and forcing it through the tubing 15 by squeezing the flexible teat 14 (with the device assembled). A rinse solution can then be passed through the tubing 15 in a like manner. The compact nature of the device, however, coupled with relatively inexpensive fabrication materials, is intended to render the supplemental breastfeeding device of the present invention disposable to the consumer.

An adjustable cord 19 can be advantageously provided (FIG. 1) to suspend the device 10 in place on the user's chest. A clamp or clip 23 which is looped through a rubber band 27 or similar resilient band, or the like, fitted around the exterior of the container 11 can be used to attach the device to the cord 19, or alternatively can be used to attach the device to an article of clothing. The clip 23 has a pair of jaws which are biased into engagement with each other, here by the natural resiliency of the plastic clip material. The preferred location for the device is with the bottom of the teat at or below the level of the breast nipples. This serves to reduce any gravity feed which might occur if the device was located higher, and assures that only suckling will draw supplement from the container.

A tubing clamp 29 is also advantageously provided. The tubing clamp 29 has an elliptical flat piece of plastic for its base, with two holes 29*a* formed therein through which the tubing 15 is threaded. The clamp 29 is carried on the tubing in this fashion, and can be slid along the tubing. A portion 31 extending from the surface of the base has a v-shaped notch 31*a* sized such that the flexible tubing 15 can be wedged therein and pinched closed (FIG. 1), such as when not in use. It will be noted that the clamp 29 would ordinarily be located further away from the nipple than is shown in FIG. 1.

Thus, while the invention has been described in connection with a certain presently preferred embodiment, those skilled in the art will readily recognize many modifications of structure, arrangement, portions, materials, and components which can be used in the practice of the invention without departing form the principles of the invention.

What is claimed is:

1. A device for delivering a liquid diet supplement to a nursing infant's mouth simultaneously with normal breastfeeding comprising:

a container for holding the liquid supplement, said container having a neck portion defining an opening at one end which is downwardly directed during breastfeeding, said container being otherwise closed;

a fluid delivery mechanism mounted on said container to close said opening, said mechanism having a flexible teat with an interior and an exterior and an opening through which an elongated flexible tube extends, said teat interior defining a reservoir for liquid supplement from said container, said tube having one end extending into said teat and in fluid communication with the interior of said teat, and another end of said tube being sized to fit into the infant's mouth simultaneously with a breast nipple, and a valve device between said container and said teat which valve device permits fluid to flow from said container into said teat but substantially prevents fluid flow back into said container from said teat, said teat when squeezed applying force to liquid supplement in said reservoir and delivering liquid supplement from said reservoir through said tube.

2. The breastfeeding device of claim 1 wherein said valve comprises a disk-shaped base sized to cover the opening of the container, and having at least one aperture in said base, and a flexible member attached to and in facial engagement with said base covering said aperture.

3. The breastfeeding assistance device of claim 1 further including a tubing clamp comprising a base portion having at least two apertures through which said elongated flexible tube is threaded, and further having a portion with a notch formed therein within which notch said tube can be wedged and pinched shut when not in use.

4. A fluid delivery mechanism for use in providing a liquid diet supplement to a nursing infant's mouth simultaneously with normal breastfeeding, comprising:

a flexible teat having an interior and an exterior;

a container for holding the liquid supplement, said container having an interior and a mouth defining an outlet from said container interior;

a collar surrounding said teat and means associated with said collar for attaching said collar and teat to said container mouth with said teat over said container outlet;

a flexible tube having a small internal diameter, said tube having one end extending into said teat and in fluid communication with the interior of said teat, and another end of said tube being sized to fit into the infant's mouth simultaneously with a breast nipple, and a valve device between said container outlet and said teat which valve permits fluid to flow from said container into said teat but substantially prevents fluid flow back into said container from said teat, said teat when squeezed applying force to liquid supplement in said reservoir and delivering liquid supplement from said reservoir through said tube.

5. The fluid delivery mechanism of claim 4 wherein said flexible teat and collar are formed integral with each other.

6. The fluid delivery mechanism of claim 5 wherein said valve comprises a disk-shaped base sized to cover said opening of said container with a plurality of apertures formed in said base, and a flexible disk-shaped member in facial engagement with the base covering said apertures, said disk-shaped member being removably attached to said base by means of a knob extending outwardly from said disk-shaped member which is received in a knob hole in said base.

7. The fluid delivery mechanism of claim 4 wherein said supplement container comprises a flexible plastic bag.

8. The fluid delivery mechanism of claim 4 wherein said supplement container comprises a noncollapsible container having a neck portion terminating in said mouth, and a vent provided to said container interior for airflow to said container interior in response to fluid flow from said container into said teat.

9. A device for feeding a liquid supplement to a nursing infant's mouth simultaneously with normal breastfeeding comprising:

a container for holding the liquid supplement therein, a liquid delivery mechanism in fluid communication with said container through a liquid channel for controlling outflow of liquid supplement from said container and delivery of the supplement to the infant's mouth at a breast nipple, said delivery mechanism including a flexible member having a hollow interior chamber forming a reservoir for liquid supplement from said container, an elongated tube having two ends one end of which is in fluid communication with said reservoir and the other end of which is sized to fit into the infant's mouth simultaneously with the breast nipple, and a one-way valve device located between said container and said flexible member in said liquid channel which valve device permits liquid to flow from said container through said channel into said flexible member chamber but substantially prevents liquid flow back into said container from said flexible member chamber, said flexible member when squeezed applying a force to said liquid supplement in said reservoir to move said liquid supplement under pressure of said force into and through said tube to thereby deliver liquid supplement to the infant's mouth at the breast nipple.

10. A device for feeding a liquid diet supplement to a nursing infant's mouth simultaneously with the infant feeding at a woman's breast, comprising:

a container for holding the liquid supplement therein, said container having an opening forming a liquid outlet;

means for supporting said container on a mother's torso with said opening located downwardly such that liquid in said container pools at said opening under the influence of gravity;

a flexible teat having a hollow interior forming a reservoir for liquid supplement from said container, said teat having an open end to said hollow interior;

means for removably affixing said teat to said container opening such that said open end of said teat is adjacent said container opening and in fluid communication with liquid in said container to thereby admit liquid to said teat hollow interior from said container;

an elongated flexible tube configured for a reduced liquid flow therethrough under influence of suckling, said tube having two ends, one end of which extends to said teat and is in fluid communication with said reservoir and the other end of which is sized to fit into the infant's mouth simultaneously with the breast nipple;

a one-way valve device located between said container outlet and said teat open end which valve device operates to permit liquid to flow from said container through said channel into said teat but substantially prevents fluid flow back into said container from said teat, said teat when compressed applying a force to said liquid supplement in said reservoir to move said liquid supplement under pressure of said force into and through said tube to thereby deliver liquid supplement to the infant's mouth at the breast nipple, said teat when released from said compression generating a suction force opening said one-way valve to liquid flow from said container, said one-way valve otherwise operating to permit liquid flow from said container into said teat under influence of a negative pressure generated by outflow of liquid from said tube, as caused by suckling; and means for admitting air into said container in response to removal of liquid from said container through said one-way valve, device.

* * * * *